United States Patent [19]

Servais et al.

[11] Patent Number: 4,795,837
[45] Date of Patent: Jan. 3, 1989

[54] STABILIZED COMPOSITIONS OF 1,1,1-TRICHLOROETHANE

[75] Inventors: Michel Servais, Kraainem; Roger Crochet, Brussels, both of Belgium

[73] Assignee: Solvay & Cie (Société Anonyme), Brussels, Belgium

[21] Appl. No.: 586,871

[22] Filed: Mar. 6, 1984

Related U.S. Application Data

[63] Continuation of Ser. No. 367,909, Apr. 13, 1982, abandoned.

[30] Foreign Application Priority Data

Apr. 13, 1981 [FR] France .................................. 81 07528

[51] Int. Cl.[4] .......................... C07C 17/42; C07C 19/05
[52] U.S. Cl. ...................................... 570/110; 570/108; 570/109
[58] Field of Search ............... 570/110, 114, 116, 108, 570/109; 252/396, 407

[56] References Cited

U.S. PATENT DOCUMENTS

| | | | |
|---|---|---|---|
| 2,567,621 | 9/1951 | Skeeters et al. | 570/110 |
| 2,870,094 | 1/1959 | Cathcart | 570/114 |
| 3,049,571 | 8/1962 | Brown | 260/652.5 |
| 3,957,893 | 5/1976 | Beckers et al. | 570/110 |
| 4,351,973 | 9/1982 | Ishibe et al. | 570/109 |

FOREIGN PATENT DOCUMENTS

| | | | |
|---|---|---|---|
| 756710 | 3/1971 | Belgium | 570/108 |
| 1284254 | 1/1962 | France . | |
| 2105205 | 4/1972 | France . | |
| 2108016 | 5/1972 | France . | |
| 2178898 | 11/1973 | France . | |
| 127404 | 11/1978 | Japan | 570/110 |
| 1319899 | 6/1973 | United Kingdom . | |

OTHER PUBLICATIONS

W. L. Archer, *Ind. Eng. Prod. Res. Dev.*, vol. 18, No. 2, pp. 131 to 135.

*Primary Examiner*—J. E. Evans
*Attorney, Agent, or Firm*—Spencer & Frank

[57] ABSTRACT

A stabilized composition of 1,1,1-trichloroethane comprising an epoxide compound, a nitro compound, and a furan compound.

17 Claims, No Drawings

STABILIZED COMPOSITIONS OF 1,1,1-TRICHLOROETHANE

This application is a continuation of application Ser. No. 367,909, filed Apr. 13, 1982, now abandoned.

BACKGROUND OF THE INVENTION

The present invention relates to stabilised compositions of 1,1,1-trichloroethane which can be used, in particular, for the degreasing of metals and for the drycleaning of textiles.

It is known that 1,1,1-trichloroethane, which is used, in particular, for the degreasing of metals and the drycleaning of textiles and in aerosols, presents a very particular problem of stability and corrosion. The use, for stabilising 1,1,1-trichloroethane, of the stabilisers normally used for other chlorinated hydrocarbons does not generally give satisfactory results. This phenomenon has been attributed in particular to the fact that 1,1,1-trichloroethane is very reactive with metals, such as aluminium, zinc and their alloys, and water. Consequently, a number and variety of specific stabilised compositions of 1,1,1-trichloroethane have been developed. Amongst these, there may be mentioned, in particular, ternary compositions based on epoxides, nitroalkanes and dioxane, described in U.S. Pat. No. 3,049,571 filed on 18.3.1960 by THE DOW CHEMICAL CO. However, none of the compositions proposed hitherto is really effective. In particular, no known composition of 1,1,1-trichloroethane has a satisfactory stability under extremely severe conditions such as those prevailing when light metals and water are simultaneously present.

SUMMARY OF THE INVENTION

The object of the present invention is to overcome the above disadvantages of the known compositions and to provide stabilised compositions of 1,1,1-trichloroethane, the stability of which is satisfactory even under the most severe conditions of use.

For this purpose, the invention relates to stabilised compositions of 1,1,1-trichloroethane comprising an epoxide compound, a nitro derivative and an internal ether, in which the internal ether is a furan compound.

DETAILED DESCRIPTION OF THE INVENTION

The term epoxide compound is understood as meaning saturated or unsaturated aliphatic compounds containing at least one epoxide group in their molecule. Preferably, the compositions according to the invention contain saturated aliphatic compounds containing from 3 to 6 carbon atoms in their molecule, such as epoxypropane, epoxybutane, 2-methylepoxypropanes, 2-methylepoxybutanes, glycidol and epichlorohydrin. Good results have been obtained with 2-methyl-2,3-epoxybutane and epoxybutane.

The total amount of epoxide compound present in the compositions according to the invention usually varies between 0.01 and 50 grams per liter. Preferably, this amount is between 0.1 and 20 grams per liter. Amounts of between 1 and 10 grams per liter are very particularly preferred.

The nitro derivatives present in the compositions according to the invention are preferably nitroalkanes containing from 1 to 4 carbon atoms in their molecule. Good results have been obtained with nitromethane, nitroethane and 1- or 2-nitropropane. Nitroethane and especially nitromethane are very particularly preferred.

The amounts of nitro compounds are the same as those defined for the epoxide compounds.

The term "furan compound" is understood as designating furan and also furan derivatives in which some of the hydrogen atoms are substituted by other atoms or radicals, and more particularly by saturated aliphatic radicals containing from 1 to 5 carbon atoms.

Generally, in the substituted derivatives, the furan nucleus is substituted by only one or two aliphatic radicals, and the substitution positions are usually on the carbon atoms in the 2- and 5-positions of the furan nucleus.

The preferred furan compounds include 2-methylfuran, 2-ethylfuran, 2-isopropylfuran, 2-propylfuran and 2,5-dimethylfuran. The best results have been obtained with 2-methylfuran, which is very particularly preferred.

The amounts of furan compound present in the compositions according to the invention generally vary between 0.1 and 100 g per liter. Preferably, this amount is between 1 and 75 g per liter. Amounts of between 5 and 50 g per liter are very particularly preferred.

Apart from the abovementioned compounds, the compositions according to the invention can contain one or more of the other stabilisers which are usual for 1,1,1-trichloroethane, such as alcohols, esters, nitriles, ketones and also heterocyclic compounds containing an oxaziridine ring in the molecule.

The alcohols can be saturated or unsaturated. The preferred alcohols contain from 1 to 7 carbon atoms and can be substituted or unsubstituted.

Usually, propanols, tertiary and secondary butanols and tertiary pentanol are used. The preferred saturated alcohols are tertiary butanol and tertiary amyl alcohol.

The unsaturated alcohols normally used are unsubstituted alcohols containing from 3 to 6 carbon atoms. Amongst these, allyl alcohol, 2-methylbut-3-en-2-ol and 2-methylbut-3-yn-2-ol are preferred. The preferred unsaturated alcohol is 2-methylbut-3-yn-2-ol.

The esters most frequently used are saturated or unsaturated monoesters and diesters containing from 2 to 8 carbon atoms, which can be substituted by halogens or hydroxyl groups. Ethyl acetate, isobutyl acetate, n-propyl acetate, methyl methacrylate and n-butyl acetate are most frequently employed. Methyl methacrylate, ethyl acetate and n-propyl acetate have proved particularly suitable.

The nitriles most frequently used are optionally substituted, saturated or unsaturated, aliphatic or aromatic compounds containing from 2 to 7 carbon atoms. Amongst these, acetonitrile, propionitrile and acrylonitrile are the most suitable.

Ketones which can be used are substituted or unsubstituted ketones containing from 3 to 7 carbon atoms, such as, for example, acetone, methyl ethyl ketone, diethyl ketone, methyl propyl ketone, methyl isopropyl ketone, 1-(furan-2-yl)-propanone, 3-hydroxyhexane-2,5-dione, 2-methyl-2-hydroxypentan-4-one and the like.

The heterocyclic derivatives containing an oxaziridine nucleus in the molecule are generally chosen from amongst 2-tert.-butyloxaziridine, 2-tert.-amyloxaziridine, 2-isopropyloxaziridine, 3-methyl-2-tert.-butyloxaziridine, 3-methyl-2-tert.-amyloxaziridine, 3-methyl-2-isopropyloxaziridine, 3,3-dimethyl-2-tert.-butyloxaziridine, 3,3-dimethyl-2-tert.-amyloxaziridine, 3,3-dimethyl-2-isopropyloxaziridine, 3-methyl-3-ethyl-2-tert.- butyloxaziridine, 3-methyl-3-ethyl-2-tert.-amyloxaziridine, 3-methyl-3-ethyl-2-isopropyloxaziridine, 3-ethyl-2-tert.-butyloxaziridine, 3-ethyl-2-tert.-amyloxaziridine, 3-ethyl-2-isopropyloxaziridine, 3-propyl-2-isopropyloxaziridine and 3-isopropyl-2-isopropyloxaziridine. Amongst these, 2-tert.-butyloxaziridine, 2-tert.-amyloxaziridine and 2-isopropyloxaziridine are the most suitable.

Other compounds can also be incorporated into the 1,1,1-trichloroethane-stabilising formulation finally used, in particular alkoxyalkanes, such as alkoxyethanes, nitrates, such as alkyl nitrates containing from 1 to 5 carbon atoms, amines, such as aliphatic amines containing from 2 to 6 carbon atoms, pyrroles, such as N-methylpyrrole, and other aromatic compounds, such as phenol and its derivatives and toluene, or other aliphatic compounds, such as diisobutylene.

The various other stabilisers used are generally present in amounts of between 0.01 and 50 g per liter and preferably in amounts of between 0.1 and 30 g per liter.

The compositions according to the invention can be used in all the applications requiring a good stability of the 1,1,1-trichloroethane. They can be used under severe conditions and in particular in the simultaneous presence of metal elements, in particular light metals, and water.

Thus, the compositions according to the invention can be saturated with water without their performance characteristics being affected. Moreover, they can also be used in contact with an aqueous phase.

The compositions of the invention also have an excellent suitability for recycling.

The examples which follow do not imply any limitation.

EXAMPLE 1

This example is given in order to show the improved stability observed with the compositions according to the invention (experiment 1), compared with other compositions of the same type (experiments 2 to 7), under severe operating conditions, that is to say in the presence of light metals and water. The results obtained in the various tests have been collated in Table 1 below.

Experiment 1

50 cm$^3$ of 1,1,1-trichloroethane, stabilised by means of 4 g/liter of 1,2-epoxybutane, 5 g/liter of nitromethane and 30 g/liter of 2-methylfuran, and treated beforehand by shaking in the presence of an equal amount of water and recovery of the 1,1,1-trichloroethane treated in this way by decantation, are introduced into a 100 cm$^3$ beaker.

Whilst keeping the mixture at ambient temperature, a 40×20×2 mm test-piece of an aluminium alloy containing 5% of copper, 1.6% of magnesium and 0.7% of manganese (AU5G1-T3 alloy) is then introduced into the mixture; after immersion in the mixture, this test-piece is scratched with a metal point, whilst keeping the test-piece under the level of the liquid during the operation.

The corrosion of the metal in the region of the scratch is then observed over a period of time; this corrosion results in the appearance of dark brown products, accompanied by the evolution of gas. To assess the results, the corrosion is referred to as extensive when it is sufficient to cause total blackening of the liquid, together with the evolution of hydrogen chloride, during the first hour. The corrosion is referred to as slight when it takes place, but without causing the phenomena described above, during the first hour. The corrosion is referred to as zero when not the slightest attack of the metal is observed for at least 12 hours.

Experiments 2, 3, 4, 5, 6 and 7

The operations of experiment 1 are repeated, but the 1,1,1-trichloroethane used is stabilised by means of 4 g/liter of epoxybutane, 5 g/liter of nitromethane and, respectively, 30 g/liter of 1,4-dioxane (experiment 2), 30 g/liter of tertiary butyl alcohol (experiment 3), 30 g/liter of 1,3,5-trioxane (experiment 4), 30 g/liter of acetonitrile (experiment 5), 30 g/liter of dioxolane (experiment 6) and 30 g/liter of methyl ethyl ketone (experiment 7).

TABLE 1

| Experiment No. | Corrosion observed | | |
|---|---|---|---|
| | Extensive | Slight | Zero |
| 1 (according to the invention) | | | X |
| 2 (comparison) | | X | |
| 3 (comparison) | X | | |
| 4 (comparison) | X | | |
| 5 (comparison) | X | | |
| 6 (comparison) | | X | |
| 7 (comparison) | X | | |

It can therefore be concluded from an examination of the results of Table 1 that the composition according to the invention (experiment 1) is the only composition not to cause corrosion after 12 hours under the severe conditions of the experiment (in the simultaneous presence of light metals and water). On the other hand, none of the known combinations (experiments 2 to 7) makes it possible to avoid slight corrosion (experiments 2 and 6) or extensive corrosion (experiments 3, 4, 5 and 7) of the metals after only 1 hour from the start of the experiment.

EXAMPLE 2

This example is given in order to show the excellent suitability of the compositions according to the invention (experiment 1) for recycling, without the addition of fresh stabiliser, compared with known compositions which are comparable thereto (experiment 2).

Experiment 1

1,400 cm$^3$ of 1,1,1-trichloroethane, stabilised by means of 4 g/liter of 1,2-epoxybutane, 5 g/liter of nitromethane and 30 g/liter of 2-methylfuran, and containing 25% of added paraffin oil, are introduced into a 2,500 cm$^3$ round-bottomed flask equipped with a condenser and connected to a supply of steam.

Steam at 110° C. is then introduced into the bottom of the flask and the mixture is steam-distilled until 99.3% of the amount of 1,1,1-trichloroethane used has been recovered.

The distillate is left to separate and 50 cm$^3$ of stabilised 1,1,1-trichloroethane are recovered and subjected to the test described in Example 1, experiment 1, without however carrying out a shaking treatment in the presence of water.

The remainder of the stabilised 1,1,1-trichloroethane is then returned to the original flask and treated in the presence of fresh paraffin oil, under the conditions described above. This operation is repeated 20 times and the corrosion caused by the various fractions collected are shown in Table 2 below.

Experiment 2

The procedure of experiment 1 is followed, but the 1,1,1-trichloroethane used is stabilised by means of 4 g/liter of epoxybutane, 5 g/liter of nitromethane and 30 g/liter of 1,4-dioxane.

The corrosion results observed with the fractions collected are also collated in Table 2.

TABLE 2

| Distillate No. | Corrosion observed | |
|---|---|---|
| | Experiment 1 (invention) | Experiment 2 (comparison) |
| 1 | zero | zero |
| 2 | " | zero |
| 3 | " | slight |
| 4 | " | slight |
| 5 | " | extensive |
| 6 | " | |
| 7 | " | |
| 8 | " | |
| 9 | " | |
| 10 | " | |
| 11 | " | |
| 12 | " | |
| 13 | " | |
| 14 | " | |
| 15 | " | |
| 16 | " | |
| 17 | " | |
| 18 | " | |
| 19 | " | |
| 20 | " | |

An examination of the results of Table 2 shows that the composition according to the invention (experiment 1) retains its stability, irrespective of the number of recycling operations to which it is subjected. The stabilising capacity of the comparison composition (experiment 2), on the other hand, is seen to be reduced after two recycling operations, so that it requires the frequent addition of fresh stabilisers.

We claim:

1. A stabilised composition of 1,1,1-trichloroethane and water comprising an epoxide compound, a nitro derivative and an internal ether, wherein the internal ether is a furan compound.

2. Composition according to claim 1, wherein the furan compound is substituted by one or two saturated aliphatic radicals containing from 1 to 5 carbon atoms.

3. Composition according to claim 1, wherein the furan compound is 2-methylfuran, 2-ethylfuran, 2-isopropylfuran, 2-propylfuran or 2,5-dimethylfuran.

4. Composition according to claim 3, wherein the furan compound is 2-methylfuran.

5. Composition according to claim 1, wherein the furan compound is present in amounts of between 1 and 75 g per liter.

6. Composition according to claim 1, wherein the epoxide compound is 2-methyl-2,3-epoxybutane or 1,2-epoxybutane, and in that the nitro derivative is nitromethane or nitroethane.

7. Composition according to claim 1, wherein the epoxide compound and the nitro derivative are each present in amounts of between 0.1 and 20 g per liter.

8. Composition according to claim 1, wherein the epoxide compound is 1,2-epoxybutane, the nitro compound is nitromethane and the furan compound is 2-methylfuran.

9. Composition according to claim 5, wherein the epoxide compound and the nitro derivative are each present in amounts of between 0.1 and 20 g per liter.

10. Composition according to claim 1, wherein the nitro derivative is a nitroalkane containing from 1 to 4 carbon atoms.

11. A composition of 1,1,1-trichloroethane and water which is stable in the presence of light metals, consisting of 1,1,1-trichloroethane, water, an epoxide compound, a nitro derivative and a furan compound.

12. The composition according to claim 11, wherein the furan compound is substituted by one or two saturated aliphatic radicals containing from 1 to 5 carbon atoms.

13. The composition according to claim 12, wherein the furan compound is selected from the group consisting of 2-methylfuran, 2-ethylfuran, 2-isopropylfuran, 2-propylfuran and 2,5-dimethylfuran.

14. The composition according to claim 13, wherein the epoxide compound is 2-methyl-2,3-epoxybutane or 1,2-epoxybutane and the nitro derivative is nitromethane or nitroethane.

15. The composition according to claim 14, wherein the furan compound is 2-methylfuran, the epoxide compound is 1,2-epoxybutane, and the nitro compound is nitromethane.

16. The composition according to claim 11, wherein the furan compound is present in amounts of between 1 and 75 grams/liter, and the epoxide compound and the nitro derivative are each present in amounts between 0.1 and 20 grams/liter.

17. The composition according to claim 14, wherein the furan compound is present in amounts of between 1 and 75 grams/liter, and the epoxide compound and the nitro derivative are each present in amounts of between 0.1 and 20 grams/liter.

* * * * *